US009593088B2

(12) United States Patent
Kostromine et al.

(10) Patent No.: US 9,593,088 B2
(45) Date of Patent: Mar. 14, 2017

(54) METHOD FOR PRODUCING A POLYMERIZABLE UV ABSORBER

(71) Applicant: BAYER MATERIAL SCIENCE AG, Leverkusen (DE)

(72) Inventors: Serguei Kostromine, Swisttal (DE); Frauke Kühn, Leverkusen (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 14/763,568

(22) PCT Filed: Jan. 29, 2014

(86) PCT No.: PCT/EP2014/051722
§ 371 (c)(1),
(2) Date: Jul. 27, 2015

(87) PCT Pub. No.: WO2014/118233
PCT Pub. Date: Aug. 7, 2014

(65) Prior Publication Data
US 2016/0002181 A1   Jan. 7, 2016

(30) Foreign Application Priority Data

Feb. 1, 2013 (EP) ..................... 13153704
Apr. 24, 2013 (EP) ..................... 13165168

(51) Int. Cl.
*C07D 251/24* (2006.01)
*C08F 2/48* (2006.01)
(Continued)

(52) U.S. Cl.
CPC .............. *C07D 251/24* (2013.01); *C08F 2/48* (2013.01); *C09D 5/32* (2013.01); *G02B 5/208* (2013.01); *G02B 5/223* (2013.01)

(58) Field of Classification Search
CPC .................... C07D 251/22; C07D 251/24
(Continued)

(56) References Cited

U.S. PATENT DOCUMENTS 5,538,840 A   7/1996  Van Toan et al.
5,869,588 A   2/1999  Toan et al.
(Continued)

FOREIGN PATENT DOCUMENTS

CN        1685008 A      10/2005
DE    102006016642 A1    10/2007
(Continued)

OTHER PUBLICATIONS

International Search Report for PCT/EP2014/051722 mailed Mar. 3, 2014.
(Continued)

Primary Examiner — Venkataraman Balasubramanian
(74) Attorney, Agent, or Firm — Drinker Biddle & Reath LLP

(57) ABSTRACT

The present invention relates to a two-stage preparation process for an organic UV absorber that has a (meth)acrylate group in the molecule and which as a result is particularly suitable for curable UV protective coatings. One example of the preparation process is:

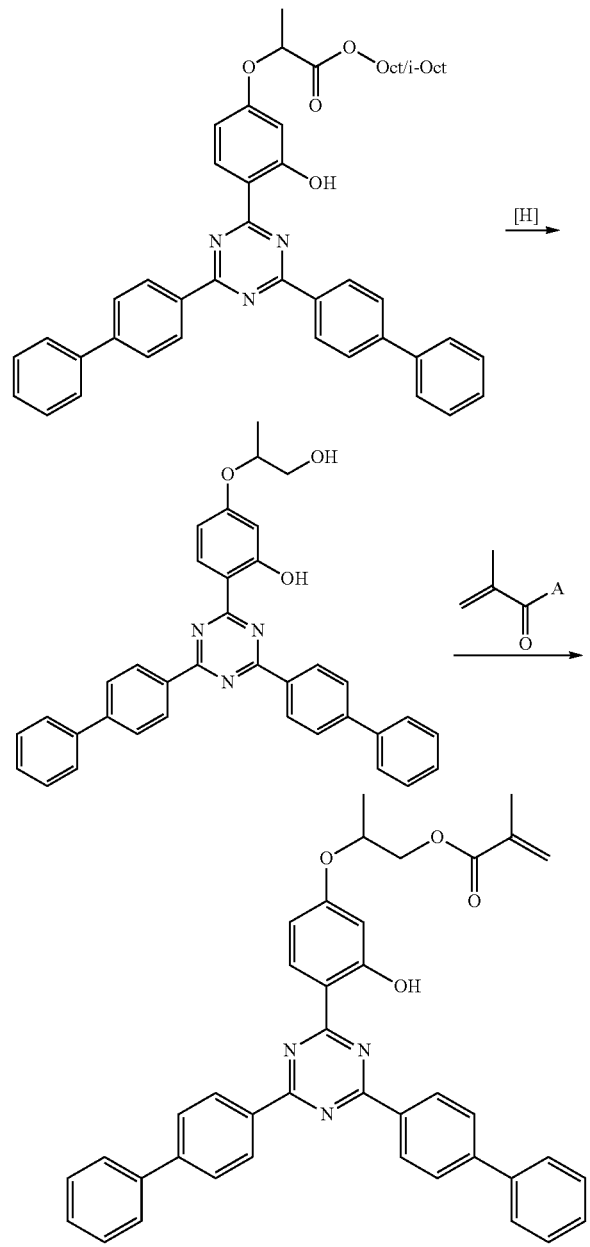

7 Claims, No Drawings

(51) Int. Cl.
  *C09D 5/32* (2006.01)
  *G02B 5/20* (2006.01)
  *G02B 5/22* (2006.01)

(58) Field of Classification Search
  USPC ........................................................ 544/180
  See application file for complete search history.

(56) References Cited

U.S. PATENT DOCUMENTS

| | | |
|---|---|---|
| 6,225,384 B1 | 5/2001 | Renz et al. |
| 7,332,105 B2 | 2/2008 | Braig et al. |
| 7,442,430 B2 | 10/2008 | Buckel et al. |
| 8,753,739 B2 | 6/2014 | Buckel et al. |
| 2012/0243115 A1 | 9/2012 | Takamiya et al. |
| 2013/0236743 A1 | 9/2013 | Kostromine et al. |

FOREIGN PATENT DOCUMENTS

| | | |
|---|---|---|
| EP | 0706083 A1 | 4/1996 |
| EP | 1094094 A1 | 4/2001 |
| EP | 2 447 236 A1 | 5/2012 |
| GB | 2293823 A | 4/1996 |
| WO | WO-00/66675 A1 | 11/2000 |
| WO | WO-2006/108520 A1 | 10/2006 |
| WO | WO-2011/040541 A1 | 4/2011 |

OTHER PUBLICATIONS

Li, L-C., et al., "Unexpected Selectivity in Sodium Borohydride Reductions of a-Substituted Esters: Experimental and Theoretical Studies", Eur. J. Chem., 2006, pp. 1981-1990.

METHOD FOR PRODUCING A POLYMERIZABLE UV ABSORBER

This application is a national stage application (under 35 U.S.C. §371) of PCT/EP2014/051722, filed Jan. 29, 2014, which claims benefit of European Application Nos. 13153704.5, filed Feb. 1, 2013, and 13165168.9, filed Apr. 24, 2013, all of which are incorporated herein by reference in their entirety.

The present invention relates to the preparation process for an organic UV absorber which has a (meth)acrylate group in the molecule and which as a result is particularly suitable for curable UV protective coatings.

For exterior applications it is necessary to protect transparent plastics articles, such as sheets, films, injection-moulded components or extrusion mouldings, for example, especially by means of UV protection, against aggressive solar radiation and, by means of scratch-proofing, against mechanical exposures. One common method for accomplishing this is to endow the top and in some cases also the only protective layer, which must be scratch-resistant, with UV protective function, additionally, and to do this by equipping it with a substantial quantity of UV absorbers (cf. DE-A 10 2006 016 642). Within the protective layers, however, the conventional UV absorbers act as plasticizers and reduce the mechanical stability of the layer.

The effect of UV absorbers on the mechanical and chemical stability of the coating increases as their concentration in the coating goes up. A certain concentration of the absorber, however, is necessary in order to absorb UV light effectively and to protect the substrate from this light reliably and durably. In accordance with the Lambert-Beer law, the thinner the coating, the greater this concentration becomes. For the modern coatings whose film thickness might be between 1 and 10 μm, this means that they ought to include up to 10 wt % of the UV absorber in order to have the necessary absorption force. As a result, the mechanical and chemical stability of such coatings is adversely affected.

One solution to the problem might be if the UV absorber were present not as a passive additive but instead as an active chemical participant in the curing process, and if it were to be tied into the polymer scaffold of the coating.

This has a positive influence not only on the hardness. The chemically bonded UV absorber cannot migrate to the outer surface of the coating and be washed off/eroded under weathering. The protective force of the coating is therefore retained as a result.

One of the best UV absorbers for polycarbonate is biphenyl-substituted triazines (cf. WO-A 2006/108520). This class of substance exhibits an outstanding absorption effect at 320-380 nm and at the same time a very high intrinsic UV stability (WO 2000/066675 A1, U.S. Pat. Nos. 6,225,384, 5,869,588).

In order to be attached to the chemical network of the coating, such molecules ought to be equipped with polymerizable acrylate and/or methacrylate groups.

Examples of such biphenyl-substituted triazines are known (EP 2 447 236 A1, WO 2011/040541 A 1). the latter international patent application discloses for example:

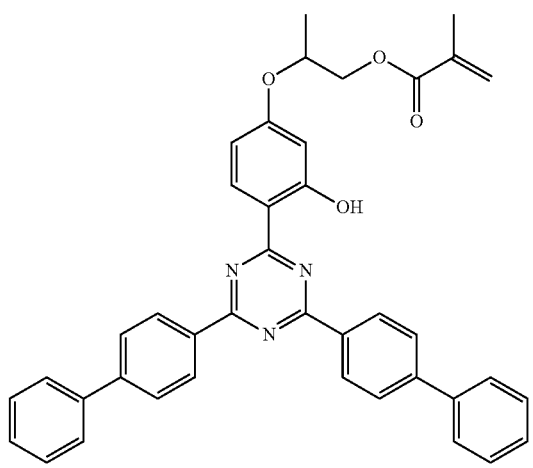 [SMILES: C=C(C)C(=O)OCC(C)Oc1ccc(-c2nc(-c3ccc(-c4ccccc4)cc3)nc(-c3ccc(-c4ccccc4)cc3)n2)c(O)c1]

In this context, simple preparation processes would be desirable for representatives of the above structures, starting from readily available feed stocks. The problem addressed by the present invention is that of providing such a preparation process.

In accordance with the invention the problem has been solved by a process for preparing compounds of a the general formula (I)

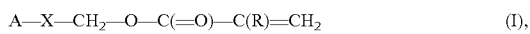

where
A is

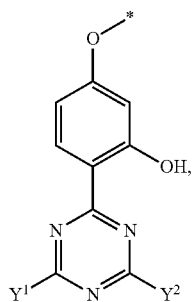

in which
$Y^1$ and $Y^2$ independently of one another are substituents of the general formula

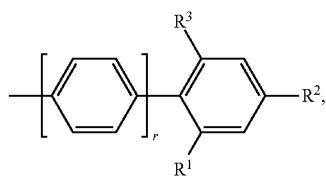

in which
r is 0 or 1, preferably 1,
$R^1$, $R^2$, and $R^3$ independently of one another are H, OH, $C_{1-20}$-alkyl, $C_{4-12}$-cycloalkyl, $C_{2-20}$-alkenyl, $C_{1-20}$-alkoxy, $C_{4-12}$-cycloalkoxy, $C_{2-20}$-alkenyloxy, $C_{7-20}$-aralkyl, halogen, —C≡N, $C_{1-5}$-haloalkyl, —SO$_2$R', —SO$_3$H, —SO$_3$M (M=alkali metal), —COOR', —CONHR', —CONR'R", —OCOOR', —OCOR', —OCONHR', (meth)actylamino, (meth)acryloyloxy, $C_{6-12}$-aryl substituted optionally by $C_{1-12}$-alkyl, $C_{1-12}$-alkoxy, CN and/or halogen, or $C_{3-12}$-heteroaryl substituted optionally by $C_{2-12}$-alkyl, $C_{1-12}$-alkoxy, CN and/or halogen, and in which M is an alkali metal cation, R' and R" are H, $C_{1-20}$-alkyl, $C_{4-12}$-cycloalkyl, $C_{6-12}$-aryl substituted optionally by $C_{1-12}$-alkyl, $C_{1-12}$-alkoxy, CN and/or halogen or $C_{3-12}$-heteroaryl substituted optionally by $C_{1-12}$-alkyl, $C_{1-12}$-alkoxy, CN and/or halogen, X is branched or unbranched $C_{1-20}$-alkyl, R is H or $CH_3$.

The process of the invention comprises the following steps:

reducing a compound of the general formula (II)

A—X—C(=O)—O—R'''       (II)

where A and X have the above definitions and R''' is branched or unbranched $C_{1-20}$-alkyl, $C_{4-12}$-cycloalkyl, or $C_{6-12}$-aryl substituted optionally by $C_{1-12}$-alkyl, $C_{1-12}$-alkoxy, CN and/or halogen;

to give a compound of the general formula (IIa)

A—X—$CH_2$OH       (IIa)

reacting the compound (IIa) obtained above with (meth)acrylic acid and/or with an anhydride, acid chloride or ester or (meth)acrylic acid.

The first step of the preparation process is a reducing of the ester group of starting compounds (I) to give a —$CH_2$—OH group. Here it is possible to use the whole range of reducing agents known to reduce an aliphatic ester group to an alcohol (C. Ferri, Reaktionen der organischen Synthese, Georg Thieme Verlag, Stuttgart, 1978, p.865).

The solvents used are specific to each reducing agent and are known to the skilled person. For aluminium hydrides they are, for example, ethers, THF, alkanes, cycloalkanes, toluene, pyridine and N-alkylinorpholine. Boranates, such as sodium boranate, are customarily employed in water, aqueous alcohol, isopropyl alcohol, acetonitrile.

The reduction of 1 mol of an ester to an alcohol theoretically uses 0.5 mol of reducing agent such as sodium boranate. In practice an excess of sodium boranate is employed. In accordance with the invention in general between 0.6 and 3 mol of reducing agent is taken for 1 mol of the starting compound, advantageously between 0.75 and 2.5 mol of reducing agent.

After the reaction the excess of the reducing agent is to be reliably deactivated before the process of destroying product intermediates with acid is commenced. In the case of the invention the excess reducing agent is deactivated by addition of simple aliphatic or cycloaliphatic ketones, which are gently consumed by reaction with the excess reducing agent. Preferred in this context is acetone, which is transformed as a result into isopropanol.

The second step of the preparation process is a (meth)acrylation of the resultant OH group of the UV absorber. The synthesis of the (meth)acrylic ester of the target compound is accomplished in accordance with the invention by reaction of the alcohol obtained above with (meth)acrylic acid or with an anhydride, chloride or ester of (meth)acrylic acid. For this purpose it is preferred to take the chloride or an ester of (meth)acrylic acid. Particularly practicable on a large scale, particularly cost-effective and hence particularly preferred is the transesterification of the alcohol with a (meth)acrylic ester.

Preferred among the (meth)acrylic esters are simple aliphatic esters of methacrylic acid, such as methyl, ethyl, propyl or butyl (meth)acrylate. Particularly preferred in this context is methyl (meth)acrylate.

To catalyse this transesterification it is possible to use acids, bases or organometallic compounds. None of the known catalysts is excluded in principle. However, advantage is possessed by the acids, and especially water-soluble acids, which can easily be removed from the crude product by washing with water. Particularly advantageous are benzenesulfonic and p-toluenesulfonic acids. For example, from 0.5 to 1.5 mol of the acid catalyst is used per mole of the intermediate (IIa).

A solvent is not always necessary in the transesterification. The (meth)acrylic ester used in excess may serve as solvent for the starting material and product. Per mole of the substance (IIa), for example, 30 to 45 mol of methacrylic ester are taken, and may be partly recovered from the reaction mixture at the end of the reaction.

An alternative to the particularly advantageous transesterification is the advantageous reacting of the substance of the formula (IIa) with methacryloyl chloride. The molar ratio of the two reactants is generally between 1:1.1 and 1:1.3. Tertiary amines or pyridine can be used as HCl scavengers. Triethylamine is advantageous. The molar ratio between the substance of the formula (IIa) and triethylamine is between 1:1.1 and 1:1,5. Examples of solvents utilized are cyclic ethers. Dioxane is advantageous.

In the starting compound (II) simple alkyl radicals are preferably selected for R''', such as methyl, ethyl, propyl, butyl, pentyl, hexyl, heptyl or octyl. Particularly suitable are n-octyl and isooctyl.

Embodiments and further aspects of the present invention are described in more detail below. They can be combined with one another arbitrarily unless the context clearly dictates the opposite.

In one embodiment of the process of the invention X is $CH(CH_3)$.

In another embodiment of the process of the invention r in each of the substituents $Y^1$ and $Y^2$ is 1.

Similarly in another embodiment of the process of the invention the radicals $R^1$, $R^2$ and $R^3$ in each of the substituents $Y^1$ and $Y^2$ are H.

Preferred for the starting compound (II) are those of the general formula (II-1):

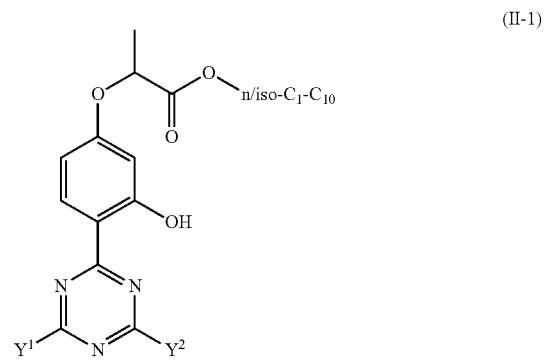

(II-1)

in which $Y^1$ and $Y^2$ have the definition stated before for the compounds of the general formula (I).

With particular preference the substituents $Y^1$ and $Y^2$ in the formulae (II) and (II-1) are simultaneously

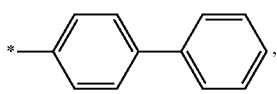

Especially preferred is the following compound as starting compound (II), which is available under the trade name Tinuvin® 479:

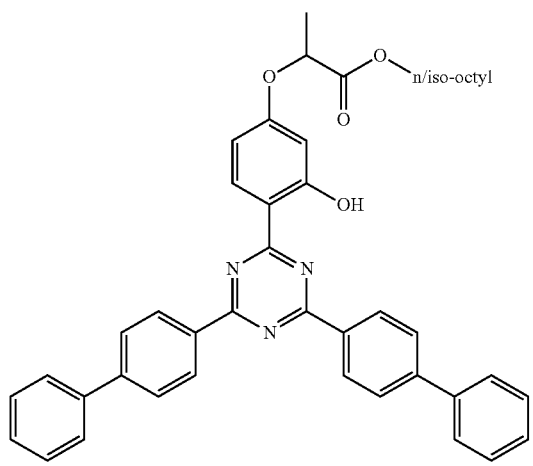

This compound (propanoic acid, 2-[4-[4,6-bis([1,1'-biphenyl]-4-yl)-1,3,5-triazin-2-yl]-3-hydroxyphenoxyl]-,n-/iso-octyl ester) is available commercially and possesses the CAS number 204848-45-3.

In another embodiment of the process of the invention the reducing of the compound (II) to the compound (IIa) takes place with a complex hydride as reducing agent. Advantageous in this context are hydrides such as aluminium hydrides, boranates such as sodium boranate or boranes or borane complexes with ethers and/or Lewis acids. Particularly advantageous is sodium boranate.

In another embodiment of the process of the invention the reducing of the compound (II) to the compound (IIa) is carried out in a solvent mixture encompassing tetrahydrofuran and an alcohol. Surprisingly it has been found that, for example, the reduction of Tinuvin 479 in accordance with the invention operates advantageously with sodium boranate in a solvent mixture of THF and an alcohol, such as methanol, ethanol, n- and isopropanol, 1-methoxy-2-propanol, n-, iso- and tert-butanol. Particularly advantageous in this regard is isopropanol.

The ratio between THF and an alcohol, such as isopropanol, in the mixture is in the range between 1:9 and 9:1, advantageously between 3:7 and 7:3, particularly advantageously between 4:6 and 6:4, based on the weight.

In another embodiment of the process of the invention the reacting of the compound (IIa) takes place with (meth)acrylic acid and/or (meth)acrylic esters and in the presence of benzenesulfonic acid and/or toluenesulfonic acid as catalyst.

EXAMPLES

The invention is described further in the following examples, but without being confined to them.

Example 1

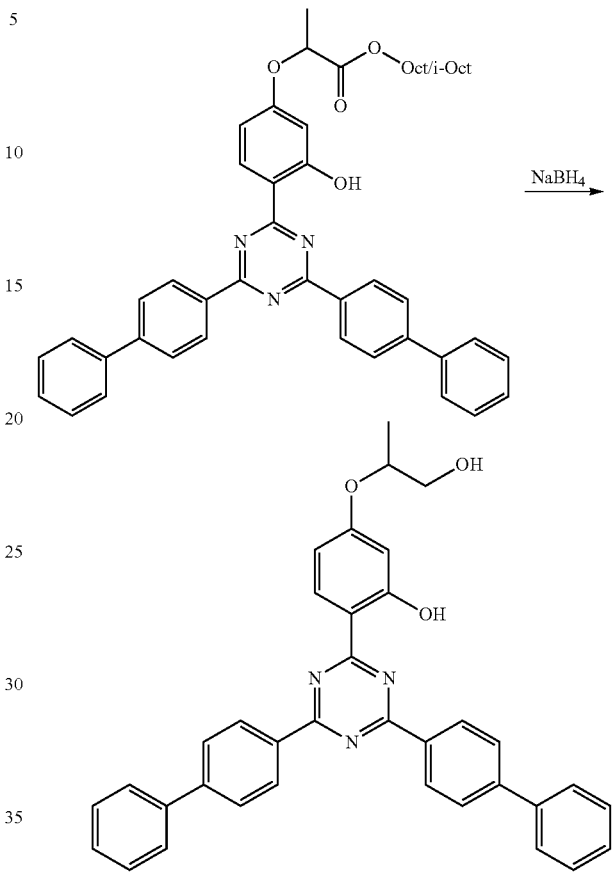

17.9 g of Tinuvin® 479 (BASF) were dissolved in 18 g of anhydrous THF at RT (room temperature) and 18 g of 2-propanol were added. 2.57 g of sodium borohydride were added (exotherm to about 50° C.) and the reaction mixture was stirred at 72° C. for 5 hours thereafter (after about 2 hours, visible formation of a precipitate: after a subsequent stirring time of 4.5 hours, addition of 18 ml of tetrahydrofuran and 18 ml of isopropanol). The course of the reaction was monitored by thin-layer chromatography with 4:1 toluene/ethyl acetate. The reaction mixture was subsequently cooled and admixed dropwise with 15.34 e of acetone (with ice bath cooling) and subsequently stirred for 45 minutes more. Thereafter, accompanied by cooling in an ice bath, 12.6 ml of 1 N hydrochloric acid were added dropwise and the mixture was stirred until gas was no longer evolved. 120 ml of methanol were then added and the mixture was stirred for 30 minutes. The solid obtained was isolated by filtration and washed on the filter with 50 ml of methanol. The solid was subsequently suspended in 120 ml of water and stirred for 1 hour. The solid was isolated by filtration (suction filter diameter: 10 cm), rinsed with 50 ml of water and 50 ml of methanol and dried at 40° C. under reduced pressure. The product was checked again with thin-layer chromatography (4:1 toluene/ethyl acetate).

Yield: 10.4 g (71.4 % of theory)
Melting point: 206° C.
Elemental analysis: $C_{36}H_{29}N_3O_3$ (551.65); calc.: C78.38; H5.30; N7.62; found: C78.10; H5.30; N7.40.

Example 2

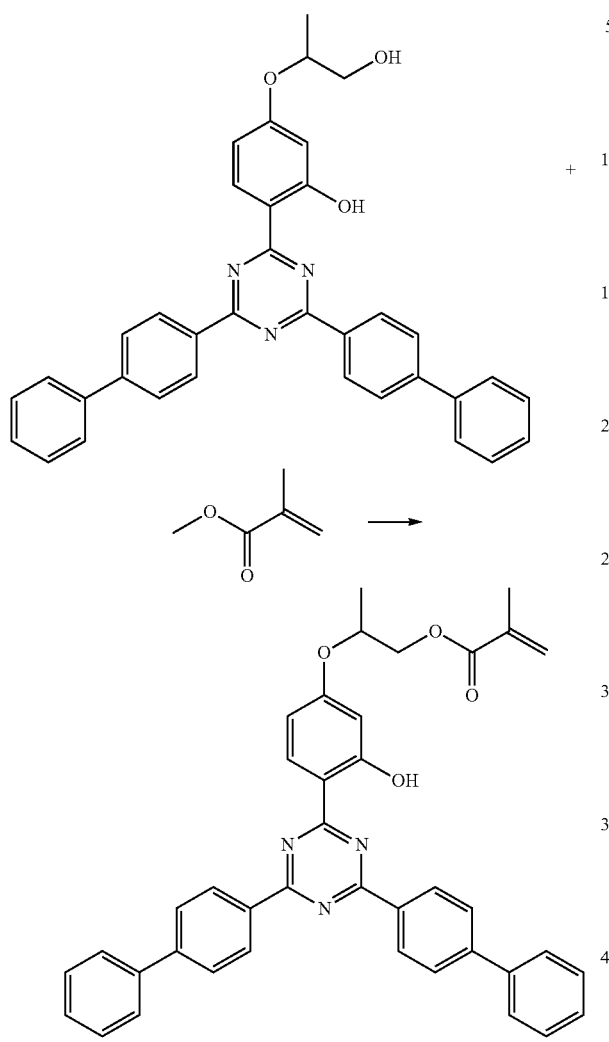

10 g of a product in accordance with Example 1, 70 g of methyl methacrylate, 5 g of p-toluenesulfonic acid monohydrate and 0.2 g of methoxyphenol were introduced together all at once into a distillation apparatus. While stirring, the oil bath was set at 120° C. Distillation began at 60° C. (overhead) and was ended at 86° C. Distillation continued until 45 g of distillate has gone over, and not beyond this point. This took about 2 hours. The reaction mixture was cooled to 40-50° C. 100 ml of methanol were added all at once to the reaction mixture, with vigorous stirring. Stirring was continued for half an hour. The crystals obtained were isolated by suction filtration, washed on the filter with methanol and dried under reduced pressure.

Yield: 12.3 g.

The crystals were dissolved in 50 ml of a 32:1 mixture of toluene/ethyl acetate and filtered through a silica gel bed 1 cm thick. Rinsing was carried out with 300 ml of a 32:1 toluenelethyl acetate mixture. Methoxyphenol (0.02 g) was added to the solution as stabilizer. The solvent was evaporated off. Methanol was added again. The crystals were isolated by filtration and dried under reduced pressure.

Yield: 6.9 g (61% of theory)

Melting point: 88° C.

Elemental analysis: $C_{40}H_{33}N_3O_4$ (619.73); calc.: C77.53; H5.37; N6.78; found: C77.20; H5.80; N6.40.

Example 2a

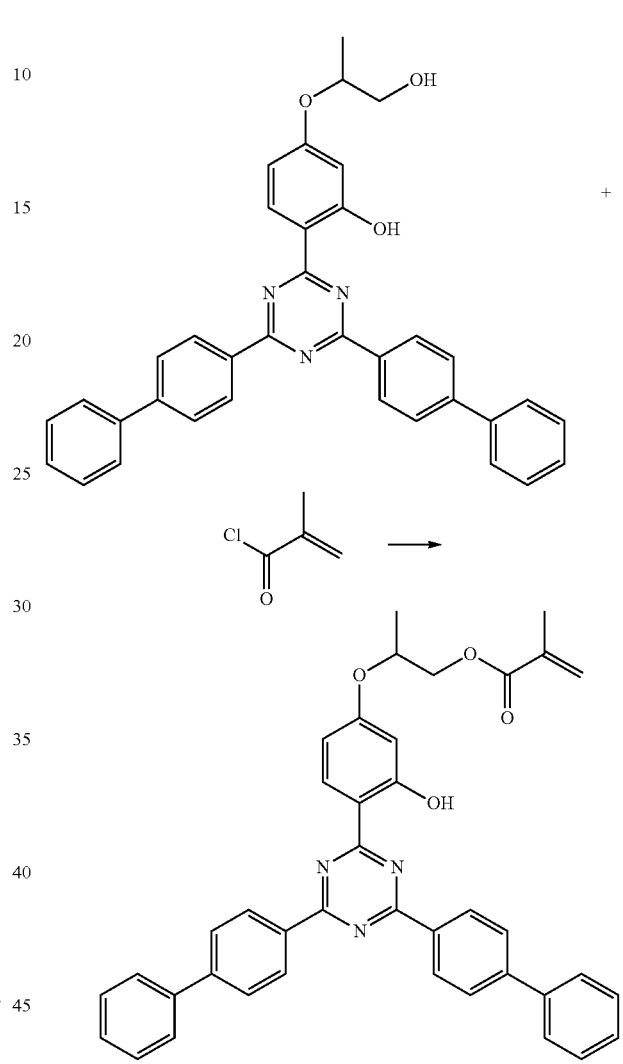

160 g of a product according to Example 1 were dissolved largely in 1100 ml of dioxane at 70° C. 45 g of triethylamine were added. The reaction mixture was cooled to room temperature. A solution of 33.3 g of methacryloyl chloride and 160 ml of dioxane was added dropwise to the reaction mixture. The reaction mixture was stirred at room temperature for 4 hours more and thereafter poured into 3 l of water. The precipitate was isolated by filtration and dried and was introduced into a mixture (8:1) of toluene and ethyl acetate. The undissolved portion (about 15 g, consisting of starting material of formula 2) was isolated by filtration, dried and used once again later for the same synthesis. The solution was filtered through a 10 cm silica gel layer. Methoxyphenol (0.02 g) was added as stabilizer to the filtered solution. The solvent was evaporated off. Methanol was added to the residue. Crystals of the target compound were isolated by filtration and dried under reduced pressure.

Yield: 100 g (56% of theory)

The invention claimed is:

1. A process for preparing a compound of formula (I)

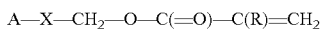   (I), where
A is

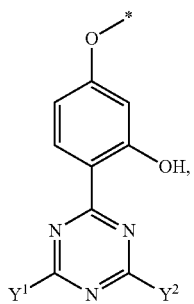

in which
$Y^1$ and $Y^2$ independently of one another are substituents of formula

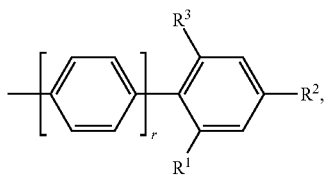

in which
r is 0 or 1, $R^1$, $R^2$, and $R^3$ independently of one another are H, OH, $C_{1-20}$-alkyl, $C_{4-12}$-cycloalkyl, $C_{2-20}$-alkenyl, $C_{1-20}$-alkoxy, $C_{4-12}$-cycloalkoxy, $C_{2-20}$-alkenyloxy, $C_{7-20}$-aralkyl, halogen X is branched or unbranched $C_{1-20}$-alkyl, R is H or $CH_3$, wherein the process comprises the following steps:
reducing a compound of formula (II)

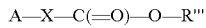   (II)

where A and X have the above definitions and R''' is branched or unbranched $C_{1-20}$-alkyl, $C_{4-12}$-cycloalkyl, or $C_{6-12}$-aryl substituted optionally by $C_{1-12}$-alkyl, $C_{1-12}$-alkoxy, CN and/or halogen;

to give a compound of formula (IIa)

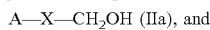   (IIa), and reacting the compound (IIa) with (meth)acrylic acid and/or with an anhydride, acid chloride or ester of (meth)acrylic acid.

2. The process according to claim 1, wherein X is $CH(CH_3)$.

3. The process according to claim 1, wherein r in each of the substituents $Y^1$ and $Y^2$ is 1.

4. The process according to claim 1, wherein the radicals $R^1$, $R^2$ and $R^3$ in each of the substituents $Y^1$ and $Y^2$ are H.

5. The process according to claim 1, wherein the reducing of the compound (II) to the compound (IIa) takes place with a complex hydride as reducing agent.

6. The process according to claim 1, wherein the reducing of the compound (II) to the compound (IIa) is carried in a solvent mixture comprising tetrahydrofuran and an alcohol.

7. The process according to claim 1, wherein the reacting of the compound (IIa) takes place with (meth)acrylic acid and/or (meth)acrylic esters and in the presence of benzenesulfonic acid and/or toluenesulfonic acid as catalyst.

* * * * *